United States Patent
Dubrovsky

(10) Patent No.: US 7,300,431 B2
(45) Date of Patent: Nov. 27, 2007

(54) REMOTE CONTROLLED DEVICE FOR TOOL ROTATING

(76) Inventor: Arkady Veniaminovich Dubrovsky, d. 11/16, kv. 27 Arkhangelsky per., 101000 Moscow (RU)

(*) Notice: Subject to any disclaimer, the term of this patent is extended or adjusted under 35 U.S.C. 154(b) by 525 days.

(21) Appl. No.: 10/518,203

(22) PCT Filed: Apr. 9, 2003

(86) PCT No.: PCT/RU03/00147

§ 371 (c)(1), (2), (4) Date: Dec. 16, 2004

(87) PCT Pub. No.: WO04/000128

PCT Pub. Date: Dec. 31, 2003

(65) Prior Publication Data
US 2005/0177138 A1   Aug. 11, 2005

(30) Foreign Application Priority Data
Jun. 24, 2002  (RU) ............................. 2002116656

(51) Int. Cl.
*A61B 17/00* (2006.01)
*F16D 3/00* (2006.01)

(52) U.S. Cl. .................. 606/1; 464/106; 464/150; 464/160

(58) Field of Classification Search .............. 606/1, 606/170–180; 285/184; 464/19, 50, 106, 464/150–160, 183; 7/165; 81/57.26–57.29
See application file for complete search history.

(56) References Cited

U.S. PATENT DOCUMENTS

| 4,071,029 A | * | 1/1978 | Richmond et al. .......... 606/180 |
| 4,641,657 A |   | 2/1987 | Ellis |
| 4,947,942 A | * | 8/1990 | Lightle et al. ............... 173/216 |
| 5,073,145 A | * | 12/1991 | Ratzokwski et al. ......... 464/157 |

(Continued)

FOREIGN PATENT DOCUMENTS

RU         2098025          12/1997

(Continued)

OTHER PUBLICATIONS

Partial English Translation of Claims of RU 2098025 dated Dec. 10, 1997.

(Continued)

*Primary Examiner*—Michael Peffley
(74) *Attorney, Agent, or Firm*—Ladas and Parry LLP

(57) ABSTRACT

A remote-controlled device for rotating tools, preferably medical tools, comprising a hollow body (1) which is embodied in the form of pivotally connected proximal and distal parts (2, 6) provided with a pair of adjacent end surfaces (5, 5') which are angularly disposed with respect to the longitudinal axis of the body (1), and an axis (7) which is perpendicularly oriented with respect to the end surfaces (5, 5') and provided with a central channel and a remote control mechanism. A shaft (10) arranged in the central channel of the device comprises driven, driving and transmitting sections (11, 12, 13) respectively, and operates as a link for transferring working rotational motion at a variable angle. The tilt angle between the distal part (6) and the longitudinal axis of the proximal part (2) can be equal to 180°.

10 Claims, 7 Drawing Sheets

U.S. PATENT DOCUMENTS 5,549,634 A * 8/1996 Scott et al. .................. 606/170
6,050,989 A * 4/2000 Fox et al. ...................... 606/1

FOREIGN PATENT DOCUMENTS

| RU | 2144791 | 1/2000 |
| RU | 2181566 | 4/2002 |
| SU | 1489731 | 6/1989 |

OTHER PUBLICATIONS

Partial English Translation of Claims of SU 1489731 dated Jun. 30, 1989.
Partial English Translation of Claims of RU 2144791 dated Jan. 27, 2000.
Partial English Translation of Claims of RU 2181566 dated Apr. 27, 2002.

* cited by examiner

REMOTE CONTROLLED DEVICE FOR TOOL ROTATING

FIELD OF INVENTION

The present invention relates generally to instrument making field, namely, to a remote controlled device for tool rotating, more precisely, for medical tool rotating.

DESCRIPTION OF RELATED ART

Remote controlled devices for tool rotating that enable to adjust a tilt angle of the tool body with respect to the longitudinal axis are well known in the art. However, in almost all conventional devices a link for transferring a working motion from a control handle to a working unit employs a flexible tie (usually a cable) or a pusher.

There have been proposed flexible rotating shafts for transferring a working motion to an operating unit of the device. But in those devices due to the inherent elasticity characteristics of a flexible shaft the application of force in transferring a motion results in some losses in operation. Furthermore, mechanic cleaning or washing the flexible shaft (as well as a flexible cable) from biological fragments and subsequent sterilisation thereof is substantially impeded.

The state of the art of devices for tool rotating designed to remote-control the position of an operating unit is well represented in the following patents:
RU, A, 2098025, RU, A, 2144791, RU, A, 2181566.

In particular, RU, A, 2098025 discloses a device for remote-controlling tool rotating which comprises a hollow body with at least two parts pivotally connected with their adjacent chambered end surfaces—a proximal part which is formed of two coaxial oriented hollow cylindrical elements designed to rotate with respect to each other—and a distal part with a tool, said hollow body also comprises a link made as a flexible cable and designed to transfer a working motion from a control handle to a tool at the distal end of the body. The outer cylindrical element in the proximal part in that device is connected to the tilted distal part of the body by means of an eccentric rotation rod.

The construction of the device body complies with all necessary requirements—the body can be of any length, any shape, the diameter thereof is easily variable within the significant range and the distal part tilt can be fixed. With all that the body structure always retains sufficient rigidity.

Tilt takes place in a space-spherical zone and the maximal tilt angle between the distal part and the longitudinal axis of the proximal part of the body can be equal to $180-2\alpha$, where $\alpha$—angle between the adjacent chamfered end surfaces and the longitudinal axis of the tool. For example, at $\alpha=45°$ the maximal tilt angle is equal to $90°$ and at $\alpha=20°$ the tilt angle is increased up to $140°$.

In the second patent cited, RU, A, 2144791 the maximal tilt angle is equal to $4\times(90-\alpha)$. For example, at $\alpha=67.5°$ the maximal tilt angle is equal to $90°$, and at $\alpha=45°$ the maximal tilt angle amount to $180°$.

In the device disclosed in RU, A, 21811566 the tilt angle at equal $\alpha 1$ and $\alpha 2$ and different values is calculated according to formulae $360-2(\alpha 1+\alpha 2)$.

The body is demountable, can be easily washed and sterilised. Furthermore, it completely embraces a located in the central channel link transferring a working motion, and thus, prevents surrounding tissues from being injured.

The use of a flexible shaft or a cable which are not easy to wash and sterilise in the above mentioned arrangements is not advantageous. Taking into account all that it is highly advisable to provide a remote controlled device for tool rotating, which could be improved in all those aspects.

SUMMARY OF THE INVENTION

It is accordingly one object of the present invention to provide a remote controlled device for tool rotating in which a construction of a link for transferring a working motion enables to transfer a motion with minimal losses.

Another object is to provide a remote controlled device for tool rotating which enables to make cleaning and sterilisation of the transferring link safe, reliable and cost-effective, as well as less labour-consuming than in the prior art devices. The present invention is intended to satisfy those needs.

In accordance with the invention a remote controlled device for tool rotating comprises a hollow body intended to house at least two parts, which are pivotally connected with their adjacent chamfered end surfaces—a proximal part connected and associated with a control handle and formed of two coaxial oriented hollow cylindrical elements intended to rotate with respect to each other, and a distal part;

a link for transferring a working motion from a control handle to a tool at the distal end of the body. According to the invention the link for transferring a working motion is designed as a shaft comprising at least two connected sections—driving and driven and operated to change an angular position of one section with respect to the other. The connection between the driven and driven sections can be tooth-engagement with teeth, provided on the facing each other ends of the respective shaft sections. The driven and driven sections can also be pivotally connected by means of a cardan joint or a joint having equal angular velocities.

In a further embodiment of the invention the shaft comprises three sections: driving, driven and transmitting sections, the latter being positioned as intermediate and operated to transfer a rotational motion from the driving section to the driven one.

In a still further embodiment of the invention the transmitting section can be in bevel gear engagement with the driving and driven sections.

In a still further embodiment of the invention each shaft section can be formed as at least two coaxial oriented elements mounted to rotate independently of one another. In case of transferring strong motion it is advisable to employ cardan joint connections of the driving and driven sections with the transmitting one.

In a still further embodiment of the invention the body of the device comprises an intermediate part having chamfered ends and arranged between the proximal and distal parts in order to rotate with respect to them, the ends of the part being chamfered in opposite directions, each mated with a chamfered end of the respective proximal and distal parts. The transmitting section of the shaft is in-housed in the intermediate part and formed of two parts, which are in pivotal or bevel gear engagement.

In a still further embodiment of the invention a hollow cylindrical element is in-housed in the intermediate part mounted between the proximal and distal parts in order to rotate with respect to them, the ends of the intermediate part being chamfered in opposite directions, each mated with a chamfered end of the respective proximal and distal parts. The hollow cylindrical element is arranged coaxial and rotable within the intermediate part. The respective cylindrical elements in the proximal and in the intermediate parts and the distal part are being in mated tooth-engagement with the teeth provided at the facing each other end surfaces of those elements, and the transmitting section of the shaft is pivotally connected to the driving and driven sections by means of cardan joints or gears.

BRIEF DESCRIPTION OF THE DRAWINGS

The invention will be more clearly understood and the embodiments disclosed in greater detail with reference to the accompanying drawings wherein.

DETAILED DESCRIPTION OF PREFERRED EMBODIMENTS

Figure 1:
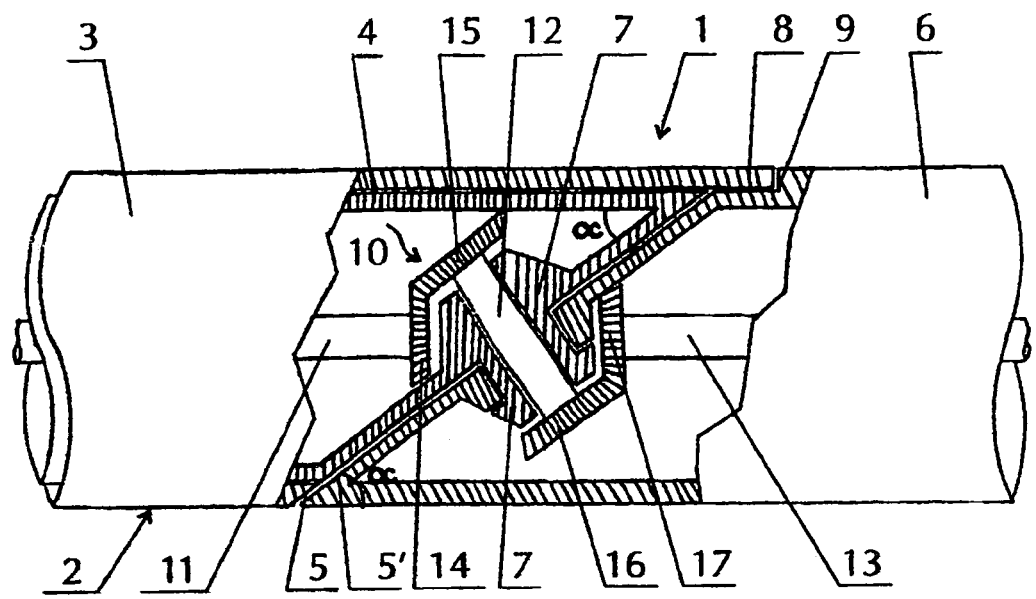
FIG. 1 is a partial profile view of the first embodiment of the device for tool rotating according to the invention as assembled.
Figure 2:
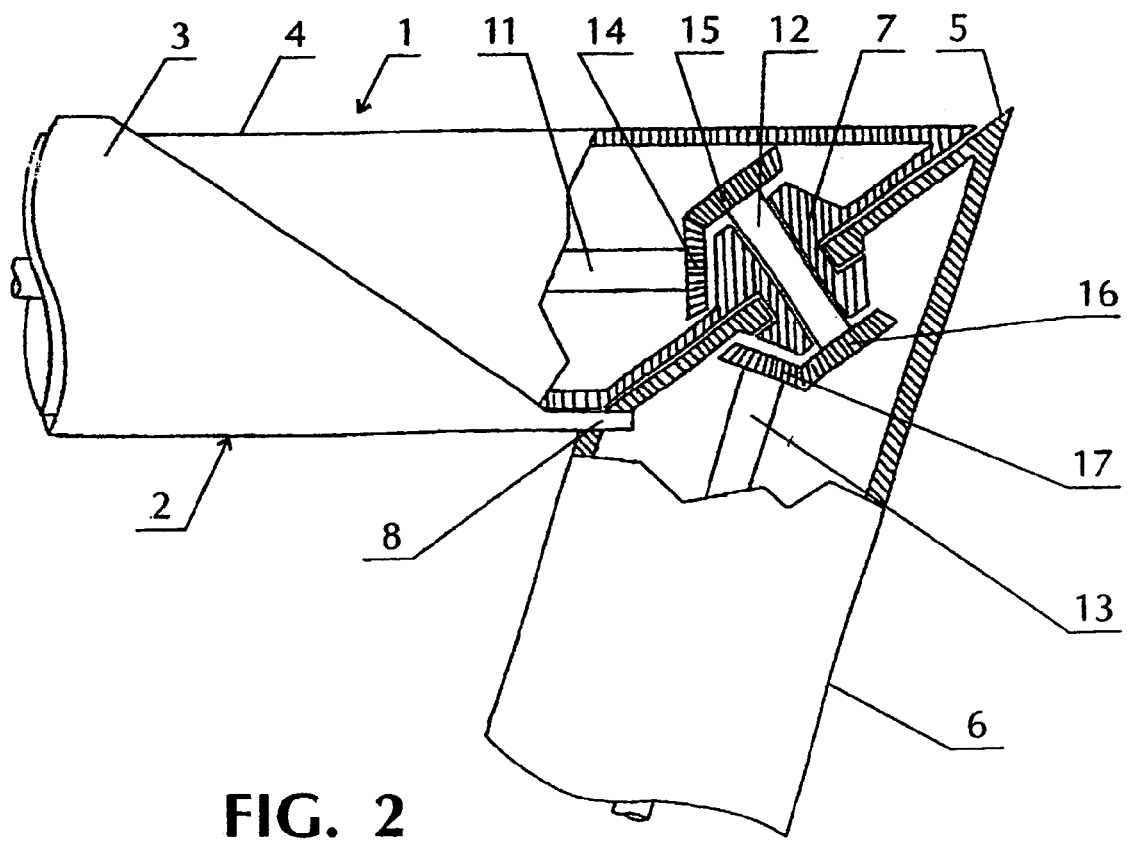
FIG. 2 is the same view as in FIG. 1 with the distal part tilted with respect to the proximal part.

Reference is now made to FIGS. 1 and 2, wherein the remote controlled device for tool rotating comprises a body 1 which proximal part 2 formed by two co-axially arranged cylindrical elements 3 and 4 has a chamfered end surface 5 which is adjacent to and mated with a chamfered end surface 5' of the distal part 6. A hollow cylindrical axis 7 is mounted in the centre of the end surfaces chamfered at the same angle α and fixed at one of the chamfered end surfaces 5. The other chamfered end surface 5' can freely rotate on the axis 7.

In the proximal part 2 the outer cylindrical element 3 has an eccentric rotation rod 8 intended to engage in a groove 9 of the distal part 6.

A link for transferring a working motion—a shaft 10 is arranged within the central channel of the device 1 and comprised of three sections: a driving section 11 of the shaft 10 located in the proximal part, a transmitting section 12 of the shaft 10 located within the central channel of the hollow axis 7 and a driven section 13 of the shaft 10 located in the distal part 6.

The driving section 11 of the shaft 10 ends with a bevel gear 14 intended to be in engagement with a bevel gear 15 fixed on the transmitting shaft section 12.

Disposed within the hollow axis 7 the transmitting section 12 of the shaft 10 at its second end has a bevel gear 16, which is intended to engage a bevel gear 17 of the driven section 13 on the shaft 10.

Said construction enables to transfer rotational motions of the driving shaft section 11 to the driven shaft section 13 at any angle possible to obtain by the device. With all that, changing the angle of rotation is being controlled remotely—as a result of rotation of the cylindrical element 3 in the proximal part 2 with respect to the cylindrical element 4 or visa versa. The construction having the transmitting section 12 on the shaft 10 makes also possible to employ it as an additional level while changing a diameter ratio of the gears 15 and 16 with respect to each other, as well as with respect to the gears 14 and 17 of the driving and driven sections 11,13, respectively on the shaft 10.

Figure 3:
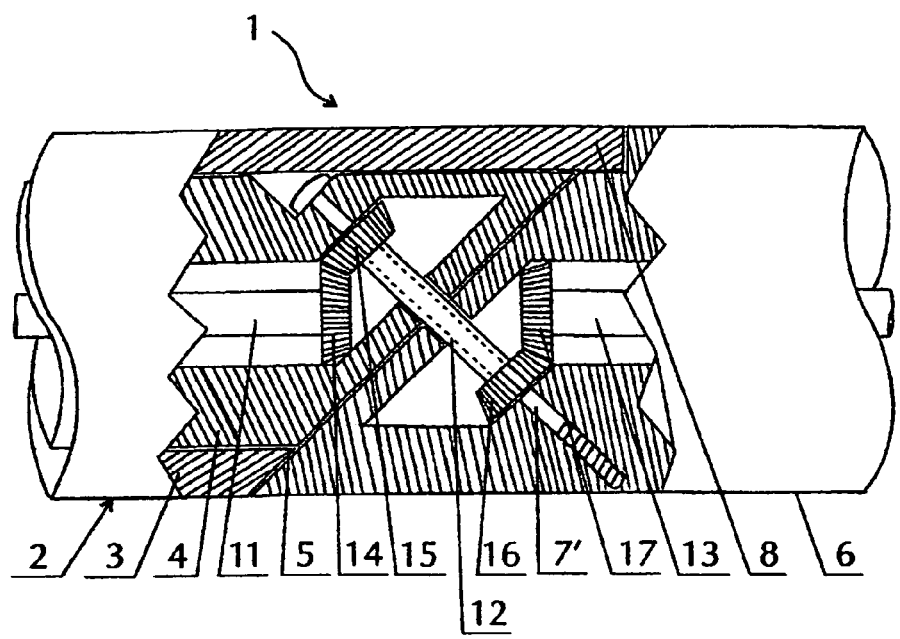
FIG. 3 is a partial profile view of the second embodiment of the device for tool rotating according to the invention as assembled.
Figure 4:
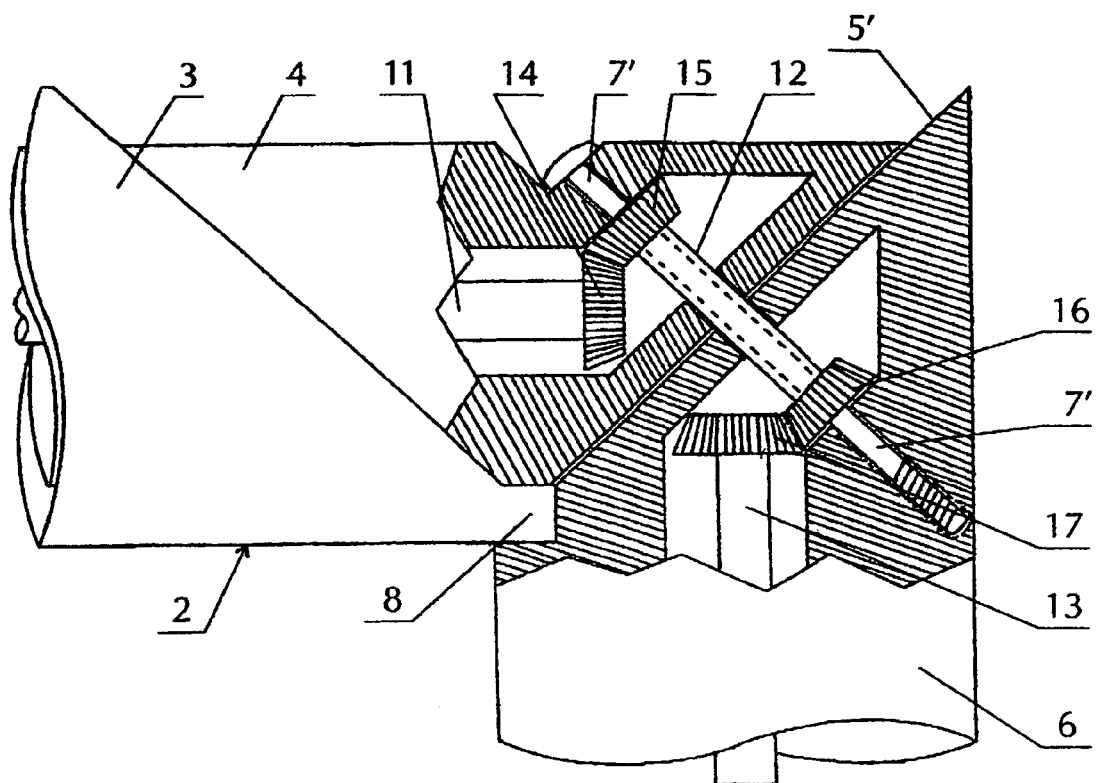
FIG. 4 is the same view as in FIG. 3 with the distal part tilted with respect to the proximal part.

The modification shown in FIGS. 3 and 4 differs from the embodiment shown in FIGS. 1 and 2 in that the pivotal connection between the proximal part 2 and the distal part 6 is provided by means of axis 7' made as a screw, which head is recessed within the inner cylindrical element 4 of the proximal part 2, and the thread end thereof is screwed into a side wall of the distal part 6. In this modification the transmitting section 12 on the shaft 10 is located on the axis 7' rather than within the same.

Figure 5:
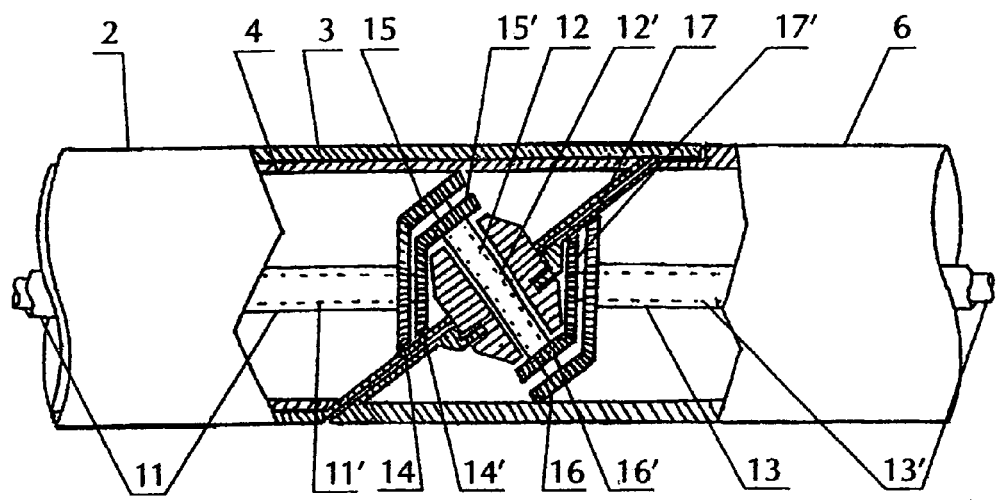
FIG. 5 is a partial profile view of the third embodiment of the device for tool rotating according to the invention as assembled arranged with two coaxial shafts.
Figure 6:
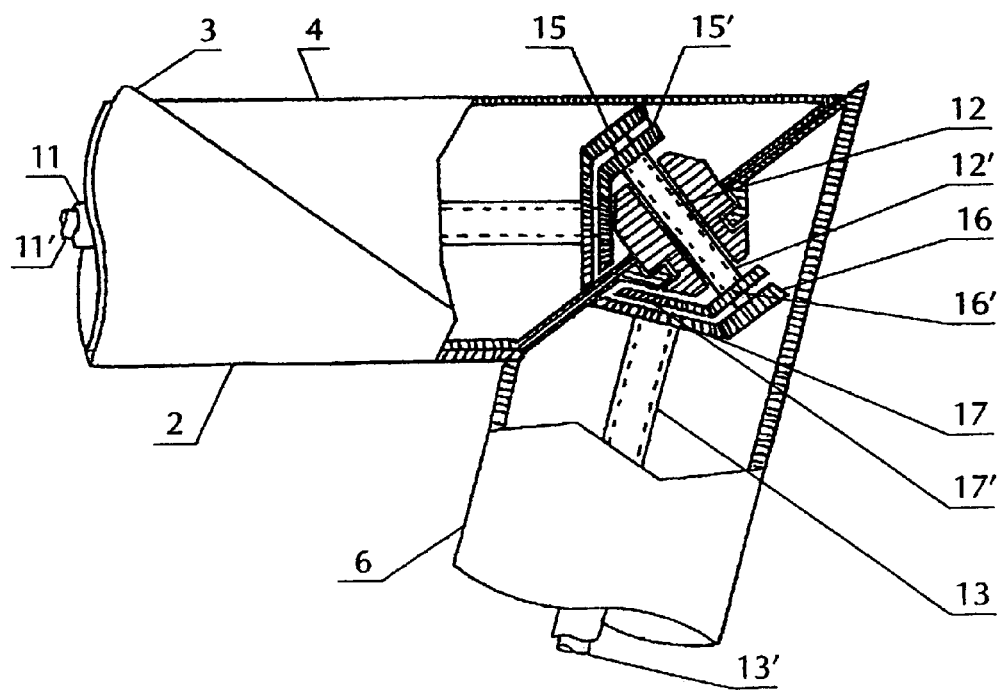
FIG. 6 is the same view as in FIG. 5 with the distal part tilted with respect to the proximal part.

In another embodiment it is possible to perform the link for transferring a working motion as at least two shaft sections each comprising two or more axial-oriented elements rotating independently of one another. It is shown in FIGS. 5 and 6, where a dotted line shows the arrangement of one shaft inside the other one: the second shaft 11' is arranged inside and in coaxial alignment with the driving section 11 of the shaft 10. Each of the shafts ends with a gear 14' and 14, respectively. The transmitting section 12 is arranged inside and in coaxial alignment with the transmitting section 12'. Each of them also has respective gears at their ends: the shaft 12 has gears 15, 16, and the shaft 12' has gears 15', 16'. Inside the driven shaft section 13 and in coaxial alignment with it there arranged the driven shaft section 13'. In its turn each of them also has a gear 17, 17' respectively. The gears mentioned are being engaged in regular relationship with respect to the appropriate shaft section—gear 14 with gear 15, gear 14' with gear 15', gear 16 with gear 17 and gear 16' with gear 17'. Such an arrangement enables each shaft to be operated independently of one another.

Figure 7:
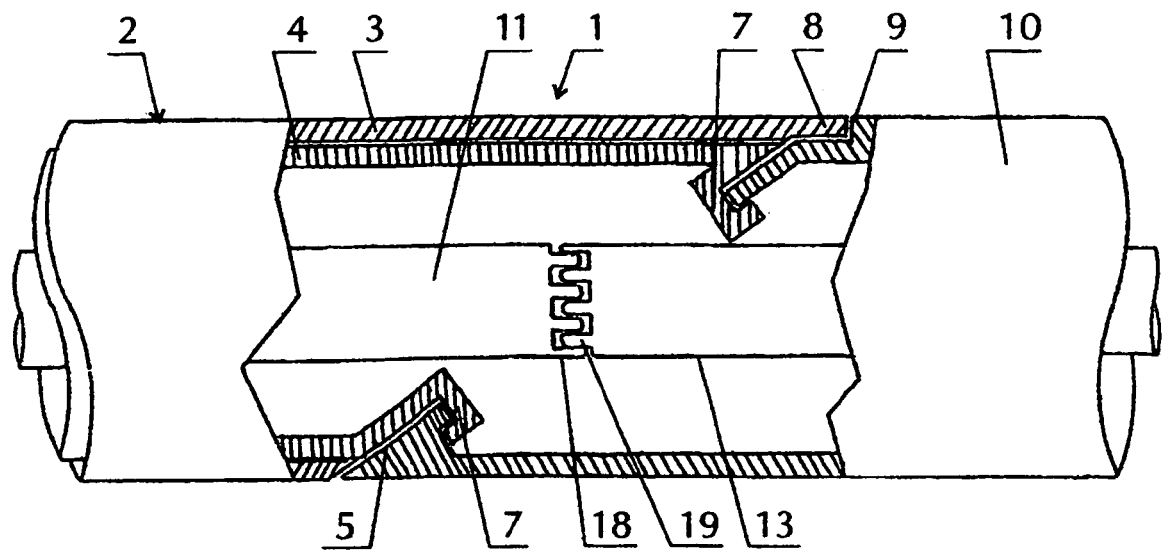
FIG. 7 is a partial profile view of the forth embodiment of the device for tool rotating according to the invention as assembled arranged with teeth at the ends.
Figure 8:
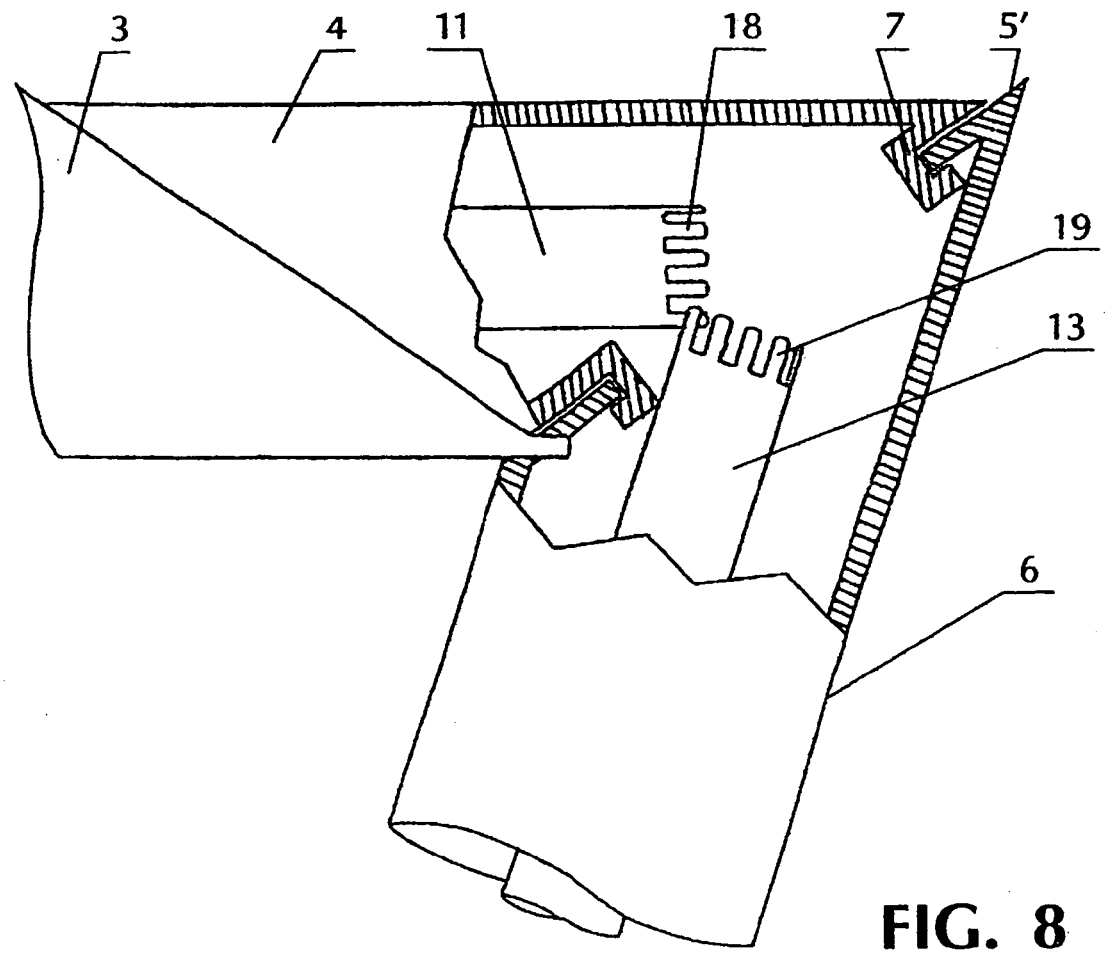
FIG. 8 is the same view as in FIG. 7 with the distal part tilted with respect to the proximal part.

Still another embodiment of the invention is shown in FIGS. 7 and 8. The link for transferring a working motion, here shaft 10 comprises two sections—driving and driven, which are engaged by means of teeth 18, 19 provided on the end facing surfaces of the respective shaft sections. Such an arrangement simplifies the construction. The tilt angle of the driven shaft section 13 in respect of the driving shaft section 11 can be increased up to 120 degrees in that embodiment (see FIG. 8).

Figure 9:
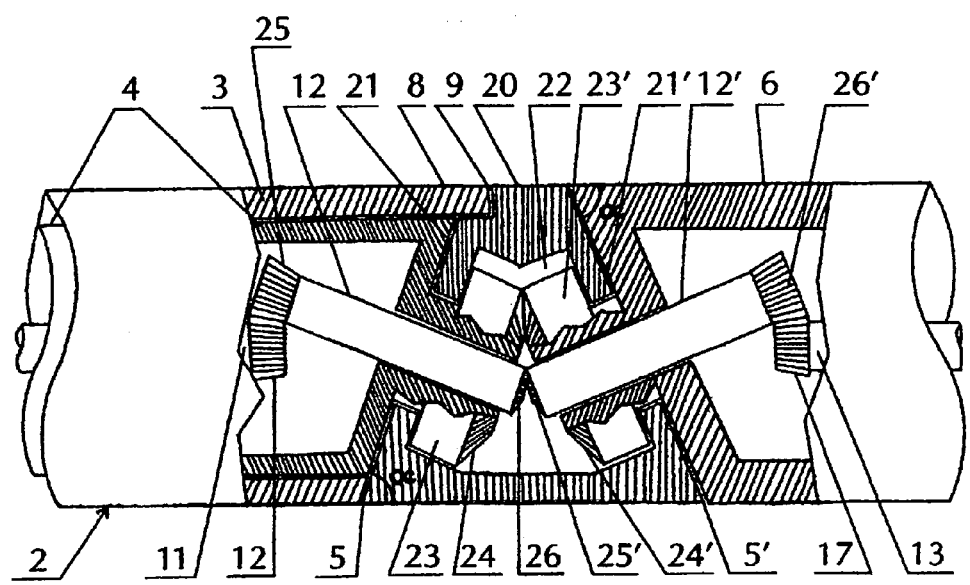
FIG. 9 is a partial profile view of the fifth embodiment of the device for tool rotating according to the invention as assembled arranged with the intermediate part in the body.
Figure 10:
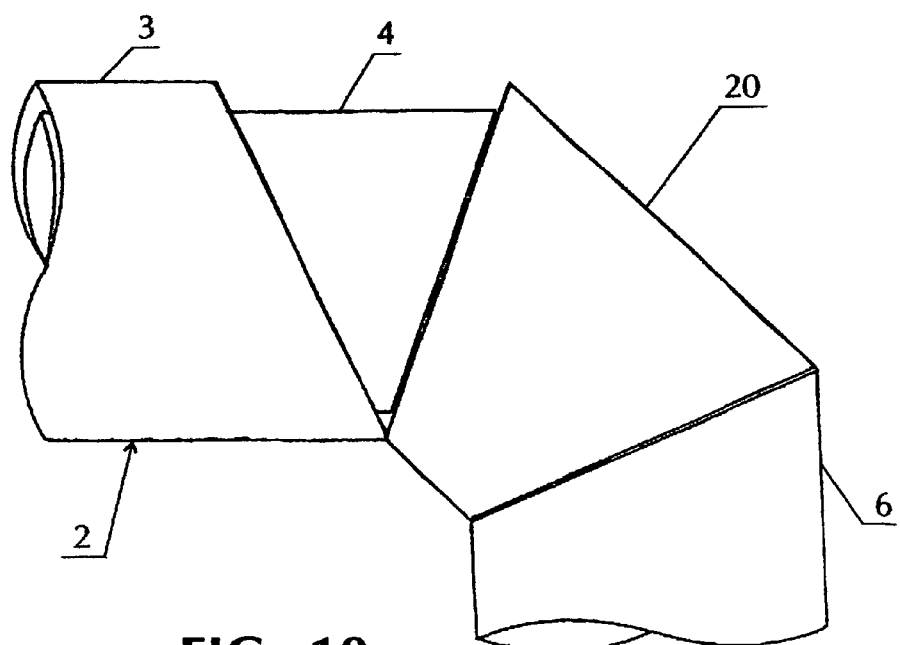
FIG. 10 is the same view of the device as in FIG. 9 in a tilted position.

In comparison to the embodiments described the modification in FIGS. 9,10 additionally comprises an intermediate part 20 between the proximal part 2 and the distal part 6. The part 20 is restricted by chamfered surfaces 21, 21', which are disposed at the same angle α with respect to a longitudinal axis of the body 1 but inclined in the opposite directions. Each of the surfaces 21, 21' is mated to come into engagement with the respective surface 5, 5' of the parts 2, 6 respectively in order to rotate the intermediate part 20 with respect to the proximal and distal parts of the body 1. The intermediate part 20 is provided with a recess 22 for axes 23, 23'. The engagement of each pair of the end surfaces 5, 21 and 5', 21' is carried out by axes 23, 23' respectively, which are perpendicularly oriented with respect to the appropriate end surfaces. Each of the axis 23, 23' is provided with a hollow central channel and ended with a bevel gear 24, 24' respectively. The teeth of the gears are in engagement relation with one another. While rotating the intermediate part 20 provides permanent engagement of the proximal part 2 and distal part 6 and deviation thereof from the longitudinal axis at the same tilt angle.

In that embodiment the central channels of the proximal 2 and the distal part 6 house the driving shaft section 11 and the driven shaft section 13 provided with gears 14, 17 at the ends thereof, and between them within the central channels of the axes 23, 23' there located two sections 12, 12' of the transmitting shaft 10, each of the sections is provided with gears 25, 26 (section 12) and gears 25', 26' (section 12') respectively at their ends. The gears 25, 26' come into engagement with gears 14, 17 respectively, the gears 26, 25' are in mutual engagement and provide transmitting the rotational motion from the driving section 11 to the driven shaft section 13.

Figure 11:
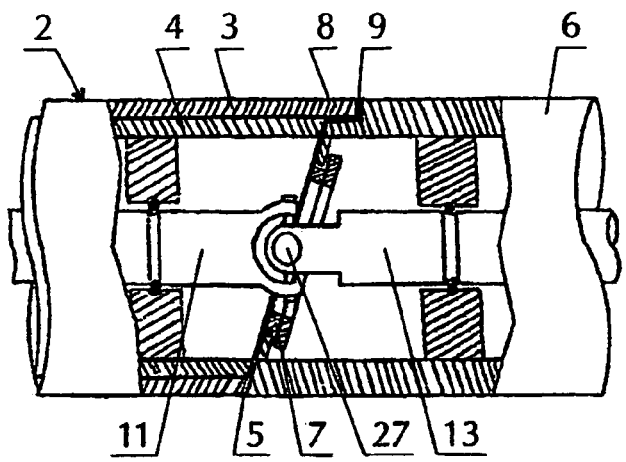
FIG. 11 is a partial profile view of the sixth embodiment of the device for tool rotating according to the invention as assembled arranged with the pivotal engagement of the driven and driving sections.
Figure 12:
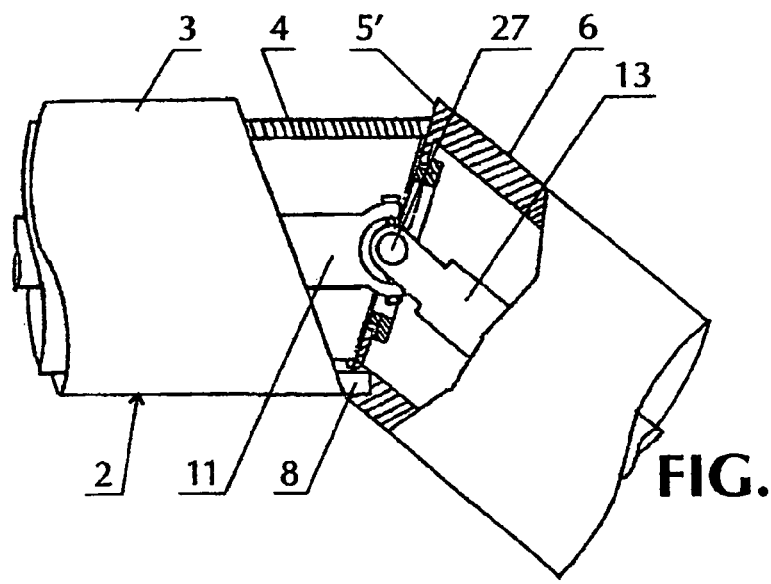
FIG. 12 is the same view as in FIG. 11 with the distal part tilted with respect to the proximal part.
Figure 13:
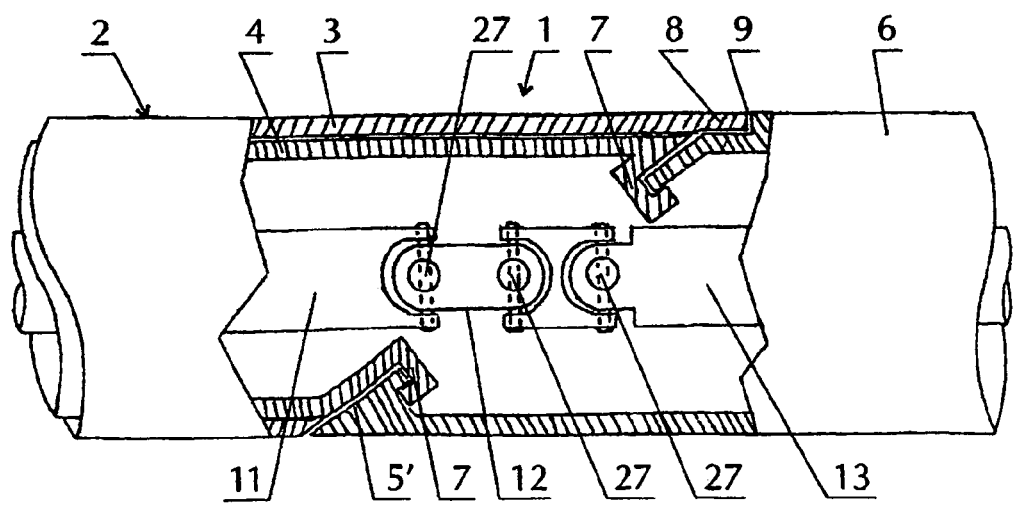
FIG. 13 is a partial profile view of the seventh embodiment of the device for tool rotating according to the invention as assembled arranged with the three joints in the transferring link.

The embodiments presented in FIGS. 11, 12, and 13 are intended to use a cardan joint. Taking into account the fact that a cardan joint transfers rotational motions smoothly only at comparatively small rotating angles, a multi-joint cardan shaft can be useful here. FIGS. 11 and 12 show the device for tool rotating which employs a single-joint cardan shaft. However, as it is shown in FIG. 13, cardan shafts with two and even three joints can be used in the device for tool rotating. Such an arrangement enables to increase a tilt angle.

Figure 14:
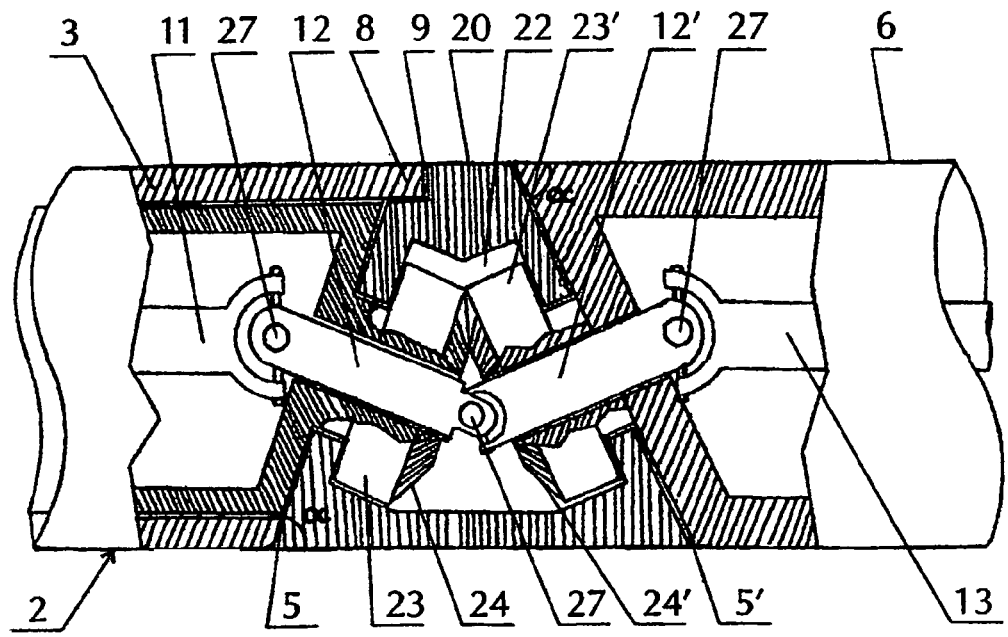
FIG. 14 is a partial profile view of the eighth embodiment of the device for tool rotating according to the invention as assembled arranged with a transmitting shaft section comprised of two parts.

The alternative device shown in FIG. 14 differs from the device shown in FIGS. 9, 10 only in that the driving section 11, the driven section 13 and the transmitting sections 12, 12' are connected in-between with three cardan joints 27.

Figure 15:
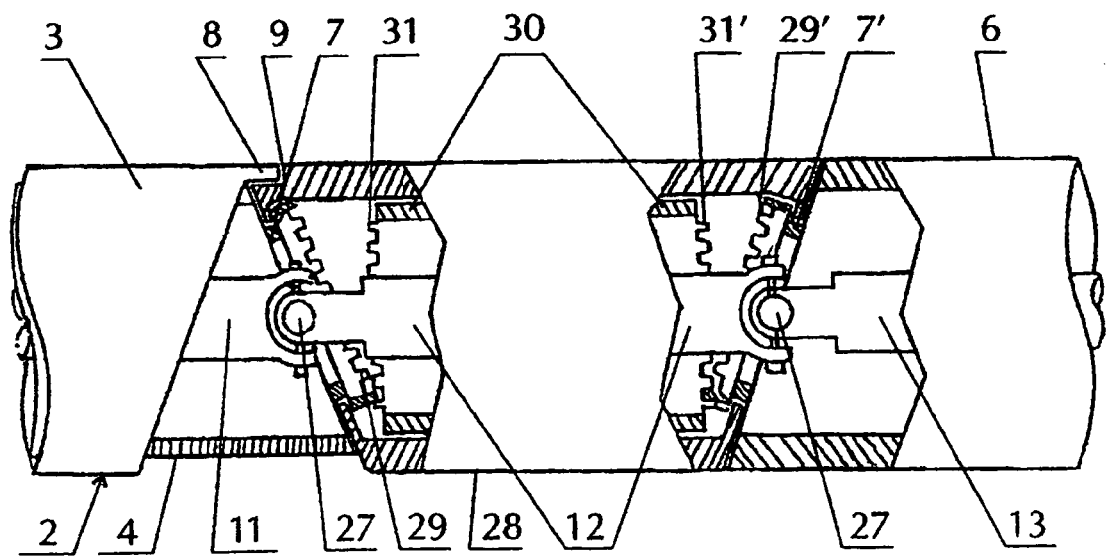
FIG. 15 is a partial profile view of the ninth embodiment of the device for tool rotating according to the invention as assembled arranged with the intermediate part and two-joint cardan shaft.

The tool rotating mechanism can employ the shaft with gears shown in FIGS. 7 and 8 or the cardan shaft with two-joint arrangement 27 as shown in FIG. 15. In this embodiment of the device an intermediate part 28 having chamfered end surfaces which are mated with chamfered end surfaces of the proximal and distal parts 2, 6 is provided between the proximal part 2 and the distal part 6 of the body 1. Unlike in the device in FIG. 14, the intermediate part 28 in this embodiment can be of any length. The hollow axes 7, 7', which are oriented perpendicularly to chamfered end surfaces and join those surfaces are provided with teeth 29, 29' at their ends. A hollow cylindrical element 30 is arranged inside the intermediate part 28 in coaxial alignment to the body 1 and provided with teeth on its end surfaces 31, 31', which teeth are intended to engage with the appropriate teeth 29, 29' provided on the end surfaces of the hollow axes 7, 7' in the proximal and the distal parts. The central channel of the body 1 houses the cardan shaft 10: the driving shaft section 11—in the proximal part 2, the transmitting shaft section 12—inside the cylindrical element 30 and the driven section 13—in the distal part 6. The driving, transmitting and driven sections 11, 12 and 13 of the cardan shaft are connected by the cardan joints 27. The operation of remote controlling the tool rotating is similar to the operation in the embodiment described above. While rotating the control outer cylindrical element 3 transfers the motion to the intermediate part 28 which rotates and tilts from the longitudinal axis, making in its turn the distal part 6 of the body 1 to tilt at a larger angle. The cardan shaft which is in-housed in the central channel of the body 1 changes its configuration accordingly. The arrangement of the cardan joints 27 is being the same as in the embodiments described above,— between the surfaces mated. In performance this embodiment of the device makes possible to obtain a smooth arc of the bend and that creates favourable conditions for the operation of the cardan shaft.

INDUSTRIAL APPLICABILITY

The remote controlled device for tool rotating as described herewith and illustrated by the embodiments is designed to transfer working rotational motions from the control handle to the tool. Said device is intended to use mainly for medicine purposes, in particular, for remote controlling surgical and stomatological tools but it may find application in other fields too.

The invention claimed is:
1. A device for remote-controlling tool rotating comprising:
a hollow body (1) including at least two parts pivotally connected with adjacent chamfered end surfaces (5, 5')—a proximal part (2) which is connected to a control handle and formed of two coaxial oriented hollow cylindrical elements (3, 4) designed to rotate with respect to each other—and a distal part (6), said hollow body (1) also including a link for transferring a working motion from the control handle to a tool at the distal end of the body, wherein said link for transferring a working motion is designed as a shaft (10) comprised of at least two sections—a driving section (11) and a driven section (13) which are connected in order to vary the angular position with respect to each other.
2. The device of claim 1, wherein the driving and the driven sections (11,13) of the shaft are connected by teeth (18, 19) coming into engagement and provided at facing end surfaces of the shaft sections (11, 13).
3. The device of claim 1, wherein the driving and the driven sections (11, 13) of the shaft are connected by means of one of joints chosen from a group consisting of a cardan joint (27) and a joint having equal angular velocities.
4. The device of claim 1, wherein said shaft additionally comprises a third transmitting section (12) which is located between said driving and driven sections (11, 13) and connected to them in order to transfer a rotational motion from the driving section (11) to the driven one (13).
5. The device of claim 4, wherein the engagement of the driving and the driven sections (11, 13) with the transmitting section (12) is provided by means of bevel gears (14, 15 and 16, 17).
6. The device of claim 5, wherein each of the driving, the driven and the transmitting shaft section (11, 12, 13) is comprised of at least two coaxial oriented elements mounted to rotate independently of one another.

7. The device of claim 4, wherein the engagement of the driving and the driven sections (11, 13) with the transmitting section (12) is provided by means of cardan joints (27).

8. The device of claim 1, wherein an intermediate part (20) having end surfaces (21, 21') chamfered in opposite directions and mated to come into engagement with the respective chamfered end surfaces (5, 5') of the proximal and distal parts (2, 6) in order to rotate with respect to the proximal and distal parts of the hollow body (1) is additionally provided in between the proximal and distal parts (2, 6) of the hollow body (1), and contains the transmitting section which is formed of two parts (12, 12') connected kinematically and designated to transfer a rotational motion.

9. The device of claim 8, wherein said kinematic connection between the parts (12, 12') of the transmitting section is provided by means of one of the systems chosen from a group consisting of a hinge joint and a bevel gear.

10. The device of claim 1, wherein an intermediate part (28) having end surfaces chamfered and mated to come into engagement with the respective chamfered end surfaces of the proximal and distal parts (2, 6) in order to rotate with respect to the proximal and distal parts is provided between the proximal and distal parts (2, 6) of the hollow body (1) and contains a hollow cylindrical element (30) arranged inside the intermediate part in coaxial alignment to the hollow body (1), said cylindrical element (4) in the proximal part (2), the cylindrical element (30) in the intermediate part (28) and the distal part (6) being engaged in between by means of teeth provided on facing end surfaces thereof (29,31 and 29', 31'), said transmitting shaft section (12) being connected with the driving and driven sections (11, 13) by means chosen from the group consisting of cardan joints (27) and gears.

* * * * *